United States Patent [19]

VandenBerg

[11] Patent Number: Plant 7,325

[45] Date of Patent: Sep. 11, 1990

[54] CHRYSANTHEMUM PLANT NAMED DAVIS

[75] Inventor: Cornelis P. VandenBerg, Salinas, Calif.

[73] Assignee: Yoder Brothers, Inc., Barberton, Ohio

[21] Appl. No.: 388,894

[22] Filed: Aug. 2, 1989

[51] Int. Cl.[5] ..... A01H 5/00

[52] U.S. Cl. ..... Plt./74

[58] Field of Search ..... Plt./74

*Primary Examiner*—James R. Feyrer

*Attorney, Agent, or Firm*—Foley & Lardner, Schwartz, Jeffery, Schwaab, Mack, Blumenthal & Evans

[57] ABSTRACT

A Chrysanthemum plant named Davis particularly characterized by its flat capitulum form, daisy capitulum type, red-purple ray floret color, diameter across face of capitulum of up to 7 cm at maturity when grown as a pinched spray pot mum, uniform nine week photoperiodic flowering response to short days, medium plant height when grown as a pinched pot mum, and spreading and prolific branching pattern.

3 Drawing Sheets

The present invention comprises a new and distinct cultivar of Chrysanthemum, botanically known as *Dendranthema grandiflora,* and referred to by the cultivar name Davis.

Davis, identified as 84-382003, was originated from a cross made by Cornelis P. VandenBerg in a controlled breeding program in Salinas, Calif., in 1983.

The female parent of Davis was an unnamed seedling identified as 80-349016. The male parent of Davis was the cultivar identified as Chic, disclosed in U.S. Plant Pat. No. 5,660.

Davis was discovered and selected as one flowering plant within the progeny of the stated cross by Cornelis P. VandenBerg on Apr. 19, 1985, in a controlled environment in Salinas, Calif.

The first act of asexual reproduction of Davis was accomplished when vegetative cuttings were taken from the initial selection in June of 1985 in a controlled environment in Salinas, Calif., by technicians working under formulations established and supervised by Cornelis P. VandenBerg.

Horticultural examination of controlled flowerings of successive plantings has shown that the unique combination of characteristics as herein disclosed for Davis are firmly fixed and are retained through successive generations of asexual reproduction.

Davis has not been observed under all possible environmental conditions. The phenotype may vary significantly with variations in environment such as temperature, light intensity and daylength.

The following observations, measurements and comparisons describe plants grown in Salinas, Calif. and Leamington, Canada, under greenhouse conditions which approximate those generally used in commercial greenhouse practice.

The following traits have been repeatedly observed and are determined to be basic characteristics of Davis, which, in combination, distinguish this Chrysanthemum as a new and distinct cultivar:

1. Flat capitulum form.
2. Daisy capitulum type.
3. Red-purple ray floret color.
4. Diameter across face of capitulum up to 7 cm at maturity, when grown as a pinched spray pot mum.
5. Uniform nine week photoperiodic flowering response to short days.

6. Medium plant height, requiring 0 to 7 long days after pinch prior to short days and 1 application of 2500 ppm B-9 SP to attain a flowered plant height of 25 to 35 cm for year-round flowerings when grown as a pinched pot mum in a 15 cm pot.
7. Branching pattern is spreading and prolific.

The accompanying photographic drawings show typical inflorescence and leaf characteristics of Davis, with the colors being as nearly true as possible with illustrations of this type. Sheet 1 is a color photograph of Davis grown as a pinched spray pot mum grown in a 15 cm pot. Sheet 2 is a black and white photograph of three views of the inflorescence of Davis. Sheet 3 is a black and white photograph showing the upper and under sides of the leaves of Davis at three stages of development (mature, intermediate and immature).

Of the commercial cultivars known to the inventor, the most similar in comparison to Davis is Circus, disclosed in U.S. Plant Pat. No. 4,188. Reference is made to attached Chart A, which compares certain characteristics of Davis to the same characteristics of Circus.

Similar traits are, capitulum form and type, diameter across face of capitulum, and plant height. Davis has a deeper, smoother flower color than Circus, and a more spreading branching pattern than Circus. Both Davis and Circus are regarded as 9 week varieties, yet Davis flowers 2 to 4 days earlier under controlled flowering.

In the following description color references are made to The Royal Horticultural Society Colour Chart. The color values were determined on plant material grown as a pinched spray pot mum in Salinas, Calif. on Apr. 6, 1989.

CLASSIFICATION:

*Botanical.*—*Dendranthema grandiflora* cv Davis.

*Commercial.*—Daisy spray pot mum.

INFLORESCENCE

A. Capitulum:

*Form.*—Flat.

*Type.*—Daisy.

*Diameter across face.*—Up to 7 cm at maturity.

B. Corolla of ray florets:

*Color (general tonality from a distance of three meters).*—Red-purple.

*Color (upper surface).*—74C to 74D.

*Color (under surface).*—70C to 70D.

*Shape.*—Straight, oblong, slightly ribbed.

C. Corolla of disc florets:

*Color (mature).*—9A.

*Color (immature).*—144B.

D. Reproductive organs:

*Androecium.*—Present on disc florets only; no pollen.

*Gynoecium.*—Present on both ray and disc florets.

PLANT

A. General appearance:

*Height.*—Medium; 25 to 35 cm as a pinched spray pot mum with 0 to 7 long days after pinch prior to short days and 1 application of 2500 ppm B-9 SP.

*Branching pattern.*—Spreading and prolific.

B. Foliage:

*Color (upper surface).*—147A.

*Color (under surface).*—147B.

*Shape.*—Deeply lobed and serrated.

CHART A

COMPARISON OF DAVIS AND CIRCUS

| CULTIVAR | DAVIS | CIRCUS |
|---|---|---|
| Ray Floret Color | Red-purple | Lavender pink |
| Capitulum Form and Type | Flat Daisy | Flat Daisy |
| Branching Pattern | Spreading and prolific | Semi-spreading |
| Diameter Across Face of Capitulum | Up to 7 cm | 57 to 70 mm |
| Plant Height | Medium | Medium |
| Controlled Flowering | 9 weeks | 9 weeks |

Comparisons Made of Plants Grown As Pinched Spray Pot Mums In Salinas, California

I claim:

1. A new and distinct Chrysanthemum plant named Davis, as described and illustrated.

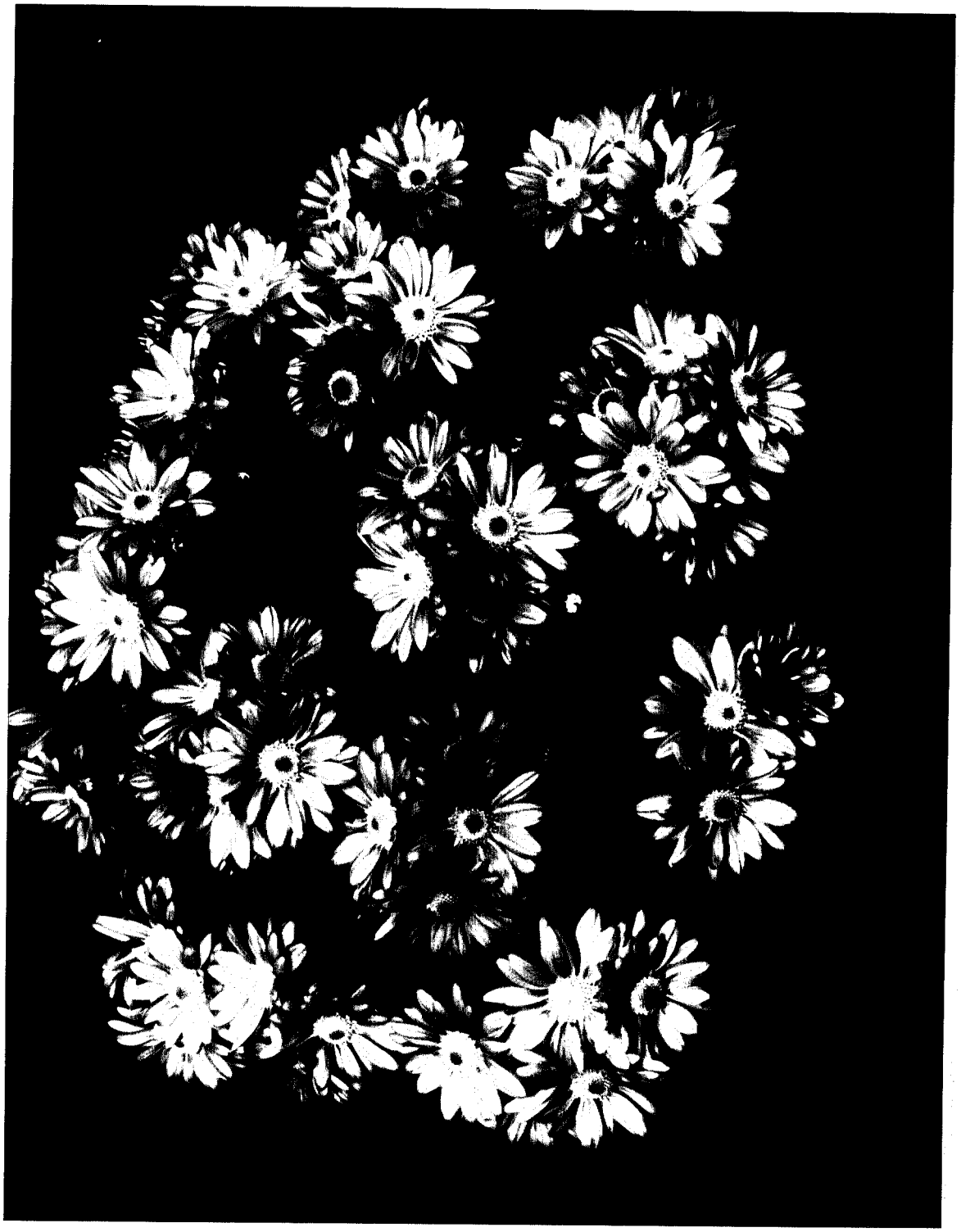

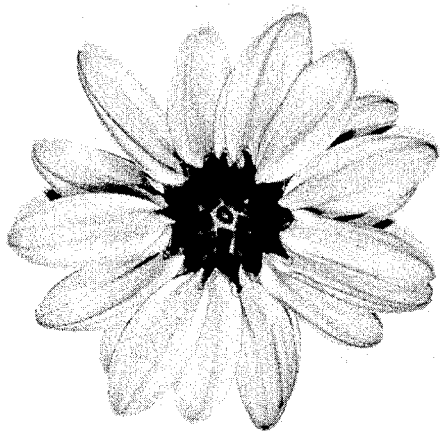
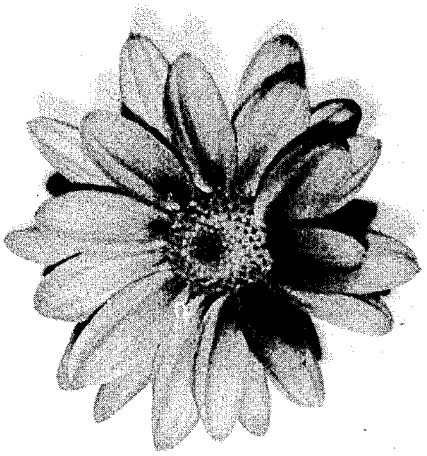
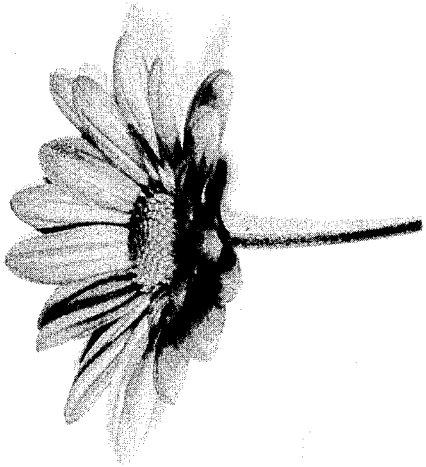

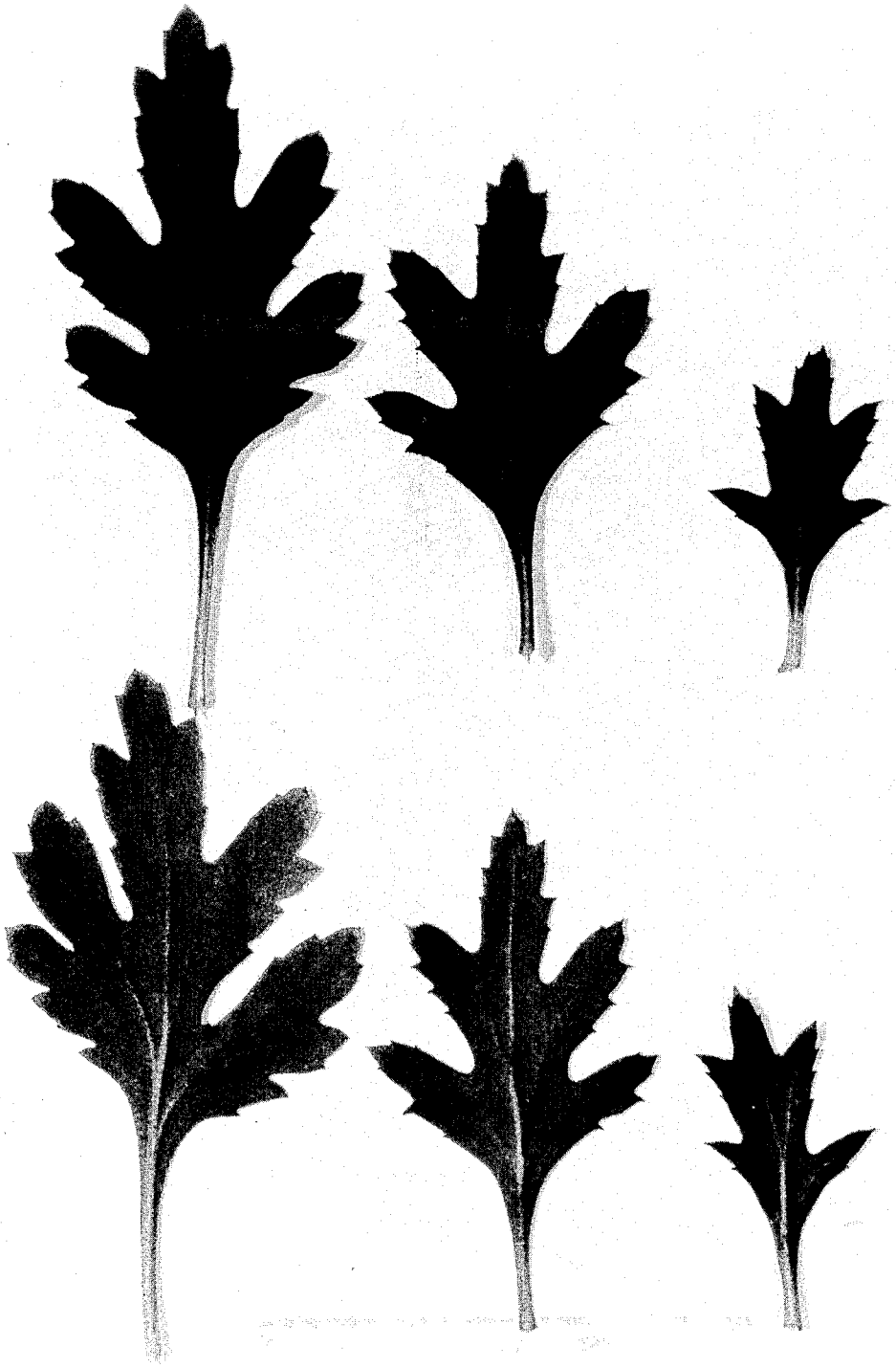

* * * * *